United States Patent
Vouland et al.

(10) Patent No.: US 7,671,041 B2
(45) Date of Patent: Mar. 2, 2010

(54) HYDROLYSATE OF AVIAN CARTILAGE, PROCESS OF PREPARATION AND USES THEREOF

(75) Inventors: Eric Vouland, Sarzeau (FR); Cäčüëline Berger, Betton (FR)

(73) Assignee: Diana Naturals, Antrain (FR)

( * ) Notice: Subject to any disclaimer, the term of this patent is extended or adjusted under 35 U.S.C. 154(b) by 918 days.

(21) Appl. No.: 11/455,239

(22) Filed: Jun. 19, 2006

(65) Prior Publication Data

US 2007/0293427 A1    Dec. 20, 2007

(30) Foreign Application Priority Data

Apr. 21, 2006    (FR) .................................. 06 03547

(51) Int. Cl.
- *A61K 31/715* (2006.01)
- *A61K 31/726* (2006.01)
- *A61K 31/728* (2006.01)
- *A61K 38/39* (2006.01)

(52) U.S. Cl. ................ 514/54; 514/62; 514/2; 536/123.1; 530/356; 530/407; 435/273; 424/548

(58) Field of Classification Search ............ 514/54, 514/62, 2; 536/123.1; 530/356, 407; 435/273; 424/548

See application file for complete search history.

(56) References Cited

U.S. PATENT DOCUMENTS

| 6,025,327 A | 2/2000 | Alkayali |
| 6,323,319 B1 | 11/2001 | Alkayali |
| 6,780,841 B2 | 8/2004 | Ishaq |

OTHER PUBLICATIONS

Eggersgluss, B., "Gelatine hydrolyste and its health aspects." *The European Food & Drink Review* (1999) pp. 45-49.

Yamato et al., "Beneficial effects of Tripeptide collagen (HACP) on bones and tendons [translation of a Japanese article]." *Foods and Foods Ingredients journal of Japan* (2005) vol. 210:9 pp. 854-858.

Blumenkrantz et al., "Hydroxyproline to hydroxylysine molar ratio indicates collagen type." *Acta Derrnatovener (Stockholm)* (1978) vol. 58 pp. 111-115.

Barnett et al. "A pilot trial of oral type II collagen in the treatment of juvenile rheumatoid arthritis." *Arthritis & Rheumatism*. (1996) vol. 39:4 pp. 623-628.

Barnett et al. "Treatment of rheumatoid arthritis with oral type II collagen." *Arthritis & Rheumatism* (1998) vol. 41:2 pp. 290-297.

Sieper et al. "Oral type II collagen treatment in early rheumatoid arthritis." *Arthritis & Rheumatism* (1996) vol. 39:1 pp. 41-51.

Trentham et al. "Effects of oral administration of type II collagen on rheumatoid arthritis." *Science* (1993) vol. 261 pp. 1727-1730.

Grés et al. "Correlation between oral drug absorption in humans, and apparent drug permeability in TC-7 cells, a human epithelial intestinal cell line: comparison with the parental Caco-2 cell line." *Pharmaceutical Research*, (1998) vol. 15:2 pp. 726-733.

*Primary Examiner*—Shaojia Anna Jiang
*Assistant Examiner*—Michael C Henry
(74) *Attorney, Agent, or Firm*—Finnegan, Henderson, Farabow, Garrett & Dunner, L.L.P.

(57) ABSTRACT

This invention relates to a hydrolysate of avian cartilage comprising 45% to 70% by weight of hydrolysed type II collagen, 9% to 15% by weight of chondroitin sulphate, 0.5% to 2% in weight of hyaluronic acid; with a composition of amino acids in which valine represents 2.7% to 3.3%, isoleucine represents 2.0 to 2.4, phenylalanine represents 2.2% to 2.6%, lysine represents 3.8% to 4.2%, tryptophane represents 0.4% to 0,6%, hydroxyproline represents 5.5% to 8.7%, hydroxylysine represents 0.7% to 1.8%, and in which the molar ratio between hydroxyproline and hydroxylysine is between 5.0 and 8.0; and having an average molecular weight of the peptidic fraction between 500 and 1000 Daltons. The invention also relates to a process for preparing said hydrolysate, and its use as a food complement, and/or as a medicament, particularly for treatment or prevention of joint pain.

7 Claims, 1 Drawing Sheet

HYDROLYSATE OF AVIAN CARTILAGE, PROCESS OF PREPARATION AND USES THEREOF

This invention relates to a hydrolysate of avian cartilage comprising 45% to 70% by weight of hydrolysed type II collagen, 9% to 15% by weight of chondroitin sulphate, 0.5% to 2% by weight of hyaluronic acid; with a composition of amino acids containing 2.7% to 3.3% of valine, 2.0% to 2.4% of isoleucine, 2.2% to 2.6% of phenylalanine, 3.8% to 4.2% of lysine, 0.4% to 0.6% of tryptophane, 5.5% to 8.7% of hydroxyproline, 0.7% to 1.8% of hydroxylysine, and in which the molar ratio between hydroxyproline and hydroxylysine is between 5.0 and 8.0; and in which the average molecular weight of the peptidic fraction is between 500 and 1000 Daltons. The invention also relates to a process for preparing said hydrolysate and its use as a food complement and/or as a medicament, particularly for treatment or prevention of joint pain.

Cartilages are highly complex tissues found in many human and animal organs. Thus, cartilages can be taken from the nasal septum, the larynx, the arterial trachea, bronchia, joint surfaces, long bone epiphyseal cartilage, the xiphoid point of the sternum, etc.

Cartilages are composed of many molecules used as active ingredients in human and animal dietetic food, in human and veterinary pharmacopoeia or in cosmetology. Some of the best known molecules include collagens, hexosamines and glycosaminoglycanes (chondroitin sulphate, keratane sulphate, hyaluronic acid).

In particular, it has been suggested that hydrolysed type II collagen, chondroitin sulphate and hyaluronic acid that form part of the constituents of the joints could be used for the treatment of joint pain. Joint pain is conventionally treated by non-steroidal anti-inflammatory drugs (NSAID) and possibly antalgic drugs, but these symptomatic treatments are often accompanied by side effects and therefore it would be useful to have treatments that could secondarily attenuate pain and improve motricity, by means of prolonged action at the joints.

Most of these molecules have been extracted from cattle cartilage for many years. However, since the appearance of bovine spongifomm encephalopathy (BSE), the food, pharmaceutical and cosmetic industries have been concerned about possible contamination of these extracts by the prions responsible for BSE, which are not inactivated by heat and are difficult to detect.

The use of chondrichthian fish skeletons could be a substitution solution for bovine derived products. But marine resources have quantitative, economic and environmental limits. Therefore it would be useful to find another source of cartilage from common animals recognised as being free from prion diseases. Domestic poultry (chicken, turkeys, ducks, guinea fowl, quail, pigeons) satisfy these health safety criteria.

U.S. Pat. No. 6,025,327 describes a material derived from cartilage of chicken sternum comprising hydrolysed type II collagen with an average molecular weight of about 1500 to about 2500 Daltons. U.S. Pat. No. 6,323,319 describes a process for obtaining the material in U.S. Pat. No. 6,025,327.

U.S. Pat. No. 6,780,841 describes a type II collagen hydrolysate capable of inducing the formation of cartilage in an individual, the said hydrolysate being obtained from cartilage of chicken sternum comprising at least 20% of depolymerised chondroitin sulphate, at least 10% of hyaluronic acid and with an average molecular weight of 5500 to about 10000 Daltons.

No results are presented demonstrating such an activity of cartilage formation, joint pain reduction or increased mobility in an individual. Furthermore, U.S. Pat. No. 6,780,841 specifically states that the proportions of depolymerised chondroitin sulphate and hyaluronic acid are essential, and that the highest possible proportions are strongly preferred, thus suggesting that a product comprising small quantities of depolymerised chondroitin sulphate and hyaluronic acid would be inefficient in vivo to induce the formation of cartilage, to reduce joint pain or to increase mobility in an individual. Furthermore, the three patents U.S. Pat. No. 6,025,327, U.S. Pat. No. 6,323,319 and U.S. Pat. No. 6,780,841 describe hydrolysates prepared solely from chicken sternum cartilage, with particularly painstaking precautions being taken to avoid including any bone, all joint cartilage being left to one side to avoid the risk of including bone fragments. These three patents very clearly indicate that the precautions to be taken for the very specific raw material used are crucial for purity of the final product to avoid contamination by type I or III collagen and thus enable the highest possible proportion of proteoglycanes.

The fact that cartilage other than sternum cartilage is not used inevitably leads to a much lower total efficiency in hydrolysate than if other cartilage was used. Furthermore, special precautions to be taken into account severely complicate use of the raw material preparation process and in particular result in it being impossible to use at the industrial scale.

Therefore it would be desirable to have a poultry cartilage hydrolysate, particularly a chicken cartilage hydrolysate, capable of inducing the formation of cartilage, reducing joint pain or increasing mobility in an individual, and that can be obtained by a preparation process appropriate for industrial use.

Unlike what is suggested in U.S. Pat. Nos. 6,025,327, 6,323,319 and 6,780,841, the inventors have demonstrated that it is possible to obtain satisfactory in vitro bioavailability and in vivo efficiency in patients suffering from joint pain, with a chicken cartilage hydrolysate comprising significantly lower proportions of depolymerised chondroitin sulphate and hyaluronic acid, the said hydrolysate also having a significantly lower average molecular weight and a significantly different composition of amino acids. Furthermore, such a hydrolysate having good in vivo efficiency can be obtained using an improved process leading to particularly appreciable gains in terms of efficiency, cost and time.

In particular, the hydrolysate developed by the inventors is obtained from a raw material containing all cartilage recoverable from a chicken carcass, and not exclusively from the sternum. The raw material used is a mix composed of 70% to 100% by weight of bone (including the sternum) and joint cartilage and 0% to 30% by weight of sternum cartilage. This raw material can be obtained without needing to use all the essential precautions described in U.S. Pat. Nos. 6,025,327, 6,323,319 and 6,780,841, and therefore be produced industrially. The global efficiency per chicken carcass is also much higher.

Furthermore, the process for obtaining the hydrolysate developed by the inventors is significantly faster than the process described in U.S. Pat. Nos. 6,025,327, 6,323,319 and 6,780,841. It does not include a step for incubation of the raw material in water, and the duration of the hydrolysis step is shorter.

Finally, unlike the process described in the U.S. Pat. Nos. 6,025,327, 6,323,319 and 6,780,841, the sterilisation step in the process for obtaining the hydrolysate developed by the inventors is carried out at the end of the protocol, which enables better health safety.

Therefore, the invention relates to an avian cartilage hydrolysate characterised in that:

a) it comprises:

45% to 70% by weight of hydrolysed type II collagen,

9% to 15% by weight of chondroitin sulphate, 0.5% to 2% by weight of hyaluronic acid;

b) among the total amino acids:

valine represents 2.7% to 3.3%, isoleucine represents 2.0% to 2.4%, phenylalanine represents 2.2% to 2.6%, lysine represents 3.8% to 4.2%, tryptophane represents 0.4% to 0.6%, hydroxyproline represents 5.5% to 8.7%, hydroxylysine represents 0.7% to 1.8%, the molar ratio between hydroxyproline and hydroxylysine is between 5.0 and 8.0;

c) the average molecular weight of the peptidic fraction is between 500 and 1000 Daltons.

Therefore the composition of avian cartilage hydrolysate according to the invention is significantly different from the hydrolysate described in U.S. Pat. No. 6,780,841. Firstly, the proportions of chondroitin sulphate (9%-15% instead of at least 20% in U.S. Pat. No. 6,780,841) and hyaluronic acid (0.5% to 2% compared with at least 10% in U.S. Pat. No. 6,780,841) are very much smaller than in the hydrolysate described in U.S. Pat. No. 6,780,841.

Such a reduction in the proportions of chondroitin sulphate and hyaluronic acid is contrary to what is suggested in U.S. Pat. No. 6,780,841, since this patent specifically states that not only the minimum proportions are 20% and 10% respectively, but also that the highest possible concentrations are preferred (see column 6, lines 49-57 in U.S. Pat. No. 6,780, 841).

Unlike what might be expected from what is described in U.S. Pat. No. 6,780,841, the hydrolysate according to the invention has an in vivo efficiency that is beneficial in patients suffering from joint pain, and at significantly lower chondroitin sulphate doses than what is generally administered. Detailed results obtained for patients suffering from joint pain are described in example 2.

Furthermore, the amino acids content in the hydrolysate according to the invention is significantly different from the amino acids content in the hydrolysate described in U.S. Pat. No. 6,780,841. Table 1 below shows comparisons of average percentages of amino acids in the hydrolysate according to the invention and in the hydrolysate described in U.S. Pat. No. 6,780,841.

TABLE 1

Comparison of amino acid contents. Data are expressed as a percentage of the raw product.

| Amino acids | Hydrolysate U.S. Pat. No. 6,780,841 Total aa | Hydrolysate according to the invention Total aa | % Difference* |
|---|---|---|---|
| Aspartic acid | 5.29 | 5.5 ± 0.5 | 3.8 |
| Threonine | 2.60 | 2.7 ± 0.3 | 3.0** |
| Serine | 2.45 | 2.4 ± 0.2 | -1.0 |
| Glutamic acid | 8.75 | 9.4 ± 0.9 | 7.6 |
| Proline | 5.25 | 6.0 ± 0.6 | 13.5 |
| Glycine | 8.93 | 10.2 ± 1.0 | 12.9 |
| Alanine | 4.51 | 5.6 ± 0.6 | 20.9 |
| Cysteine | 0.46 | 0.5 ± 0.1 | 10.3 |
| Valine*** | 2.43 | 3.0 ± 0.3 | 22.4 |
| Methionine | 1.38 | 1.5 ± 0.2 | 11.1 |
| Isoleucine | 1.90 | 2.2 ± 0.2 | 15.8 |
| Leucine | 4.20 | 4.3 ± 0.4 | 2.6 |
| Tyrosine | 1.16 | 1.6 ± 0.2 | 29.3 |
| Phenylalanine | 2.14 | 2.4 ± 0.2 | 12.5 |
| Histidine | 2.05 | 1.6 ± 0.2 | -24.8 |
| Lysine | 3.54 | 4.2 ± 0.4 | 17.5 |
| Arginine | 4.42 | 5.4 ± 0.5 | 20.0 |
| Tryptophane | 0.37 | 0.5 ± 0.1 | 36.0 |
| Hydroxyproline | 3.9 | 6.5 ± 1.8 | 50.0 |
| Hydroxylysine | absent | 1.2 ± 0.7 | |

*% difference = (average value in hydrolysate according to the invention − value in U.S. Pat. No. 6,780,841)/(average of two values) * 100
**In bold: essential amino acids
***With grey background: essential amino acids present in a significantly greater proportion in the hydrolysate according to the invention Thus, in particular the proportions of valine (+22.4%), isoleucine (+15.8%), phenylalanine (+12.5%), lysine (+17.5%), tryptophane (+36%), hydroxyproline (+50%) and hydroxylysine (not present in the hydrolysate in U.S. Pat. Nos. 6,025,327, 6,323,319 and 6,780,841) are significantly different.

Valine, isoleucine, phenylalanine, lysine, and tryptophane are essential amino acids, in other words they cannot be synthesised by the organism and therefore have to be added through food. All of the nine essential amino acids except for histidine are present in the hydrolysate according to the invention in at least equal proportions. Furthermore, five of these essential amino acids (valine, isoleucine, phenylalanine, lysine, and tryptophane) are present in the hydrolysate according to the invention in significantly greater proportions. Since this hydrolysate is used particularly as a food complement, this is another advantage of the invention.

Hydroxyproline and hydroxylysine are modified amino acids present particularly in collagen in which they play an important role in the formation of covalent bonds between different neighbouring polypeptidic chains, thus reinforcing the three-dimensional structure of collagen.

Therefore oral administration of a product that contains it provides a useful source of these amino acids for the formation of collagen (1). Furthermore, a study (2) demonstrates the beneficial effect of the Gly-Pro-Hyp collagen tripeptide (therefore containing hydroxyproline) on the bone and tendon repair process in animal models. The study also mentions that the content of hydroxyproline in the <<treated group >> is significantly closer to normal after two weeks than in the group that did not receive collagen hydrolysate.

Furthermore, the molar ratio between hydroxyproline and hydroxylysine in the hydrolysate according to the invention is between 5.0 and 8.0. The molar ratio between hydroxyproline and hydroxylysine provides a means of differentiating type II collagen from type I and III collagens (3). The ratio is about 5 for a type II collagen, while it is more than 10 for type I and III collagens. In this case, the average value of the ratio demonstrates the clear predominance of the presence of hydrolysed type II collagen. The fact that hydroxylysine was not detected in hydrolysates in patents U.S. Pat. No. 6,025,327, U.S. Pat. No. 6,323,319 and U.S. Pat. No. 6,780,841 would indicate that the molar ratio between hydroxyproline and hydroxylysine is undoubtedly fairly high, and in any case is higher than in the hydrolysate according to the invention, otherwise this amino acid would have been detected.

Thus, although the mechanisms have not been clearly defined, different studies have demonstrated that type II collagen and its elementary constituents (including hydroxyproline and hydroxylysine) have an advantage for the treatment of joint pain (4-7). Therefore, after seeing the previous analysis of the composition of the hydrolysate according to the invention, it would appear that it has a composition rich in type II collagen (ratio of the percentages of hydroxyproline and hydroxylysine close to 5), and that it has significantly high proportions of the two elementary constituents, namely hydroxyproline and hydroxylysine, than the hydrolysates in U.S. Pat. Nos. 6,025,327, 6,323,319 and 6,780,841. The advantage of such a composition of the hydrolysate according to the invention has also been demonstrated by the inventors in a double blind study with patients suffering from joint pain. (See Example 2).

Finally, the average molecular weight of the peptidic fraction in the hydrolysate according to the invention (about 700 Daltons) is significantly lower than the corresponding molecular weight of the peptidic fraction in the hydrolysate claimed in patents U.S. Pat. No. 6,025,327 and U.S. Pat. No. 6,323,319 (between 1500 and 2500 Daltons) and in patent U.S. Pat. No. 6,780,841 (between 5500 and 10000 Daltons). In patent U.S. Pat. No. 6,780,841, although the description gives a very wide range of average molecular weights (from 50 to 10000 Daltons), and although the so-called preferred average molecular weight is fairly low (column 3, lines 61-65), the optimum average molecular weight is fixed at 5500 Daltons which suggests that although a low molecular weight is preferable, the value should not be below about 5500 Daltons. This preferred average molecular weight is significantly higher than the average molecular weight of the hydrolysate according to the invention (about 700 Daltons). This lower molecular weight could be involved in improving the bioavailability of the hydrolysate according to the invention, particularly by better passage through the intestinal barrier. The inventors have used an in vitro model and demonstrated that the bioavailability of the hydrolysate according to the invention is about three times greater than a non-hydrolysed product (see example 1). The molecular weight of the peptidic fraction of the hydrolysate according to the invention was measured using a method for obtaining the distribution of proteins and other food products by molecular weight (MW) in hydrolysates. The distribution by molecular weight (MW) was obtained by a liquid phase chromatographic analysis (gel permeation). This analytic method is calibrated with a mix of standards:

beta lactoglobulin (MW=18 300 Da)
alpha-lactalbumin (MW=14 000 Da)
insulin (MW=5730 Da)
bacitracin (MW=1450 Da)
tryptophane (MW=204 Da)

The product to be analysed is diluted in the elution buffer and is then injected onto the column after filtration (0.45 µm). A software (CPG plus, TSP) specially designed for molecular weight distributions is used to obtain the molecular weight distribution of the product directly.

Furthermore, the hydrolysate according to the invention has the very important advantage that it is obtained from a much less specific raw material than the hydrolysates described in patents U.S. Pat. No. 6,025,327, U.S. Pat. No. 6,323,319 and U.S. Pat. No. 6,780,841, that use chicken sternum cartilage exclusively (see column 5, lines 6-7). On the contrary, the hydrolysate according to the invention can be obtained from a mix of chicken bone (including the sternum) and joint cartilage (about 70%-100% by weight) and possibly sternum cartilage (about 0-30% by weight). This makes it possible to use the entire chicken carcass and therefore to improve the fabrication efficiency, and also to avoid the painstaking precautions necessary according to the protocol described in U.S. Pat. No. 6,780,841 (column 4, lines 60-66), and therefore to make industrial processing of the carcasses possible, thus inducing cost and time savings.

Therefore in one advantageous embodiment, the hydrolysate according to the invention is prepared from a mix of bone and joint cartilage (70%-100% by weight) and possibly sternum cartilage (0%-30% by weight). The mix of bone and joint cartilage that represents 70% to 100% of the weight of the raw material used in the invention can be obtained from a whole chicken carcass from which the muscular tissues have been removed, and that is then ground. Finally, the sternum cartilage can possibly be added in a proportion of 0% to 30% by weight of the total raw material to obtain the raw material, without the need to take the painstaking precautions described in U.S. Pat. Nos. 6,025,327, 6,323,319 and 6,780,841 when collecting the sternum cartilage. A small contamination of sternum cartilage by bone or another type of cartilage has no incidence on the product obtained, due to the majority presence of the mix of bone and joint cartilage. For example, it would be possible to use about 75% of a mix of bone and joint cartilage and about 25% of sternum cartilage, but these percentages can be freely adjusted within the 70%-100% and 0%-30% ranges respectively, such that the total is 100%, without significantly modifying the product obtained.

Apart from the raw material, the inventors have also developed a process for obtaining the hydrolysate according to the invention, with all its particular characteristics (proportions of type II collagen, chondroitin sulphate, hyaluronic acid; content of amino acids; average molecular weight) while reducing the manufacturing time compared with the processes described in patents U.S. Pat. No. 6,025,327, U.S. Pat. No. 6,323,319 and U.S. Pat. No. 6,780,841.

Thus, the invention also relates to a process for preparing a hydrolysate of avian cartilage according to the invention, comprising:

a) supplying a raw material composed of 70%-100% by weight of bone and joint cartilage (including sternal cartilage) and 0%-30% by weight of sternum cartilage,
b) mixing this raw material with an aqueous solution with a pH between 5.5 and 7.5, c) hydrolysing the mix of raw material in water with a proteolytic enzyme during 1 h to 2 h, preferably during 1 h30 to 2 h, at a temperature between 65° C. and 75° C. and preferably between 70° C. and 72° C., d) inactivating the proteolytic enzyme for 10 to 20 minutes at at least 85° C., e) filtrating the reaction mix containing the hydrolysate, f) concentrating the reaction mix, g) performing final sterilisation of the reaction mix at about 130° C. for at least about 30 seconds and h) drying the reaction mix to obtain the hydrolysate in powder form.

This process has several advantages that do not occur with the processes described in patents U.S. Pat. No. 6,025,327, U.S. Pat. No. 6,323,319 and U.S. Pat. No. 6,780,841.

Firstly, the total manufacturing duration is significantly shorter. In the process described in U.S. Pat. No. 6,780,841, the raw material is mixed with an aqueous solution in which it is then incubated for about an hour (column 5, lines 55-56). On the other hand, in the process according to the invention, the raw material is mixed with an aqueous solution with a pH between 5.5 and 7.5, particularly such as water or brine, but the hydrolysis step is carried out without the need for prior incubation in the aqueous solution. Advantageously, hydrolysis is done immediately, or less than 15 minutes after mixing.

Furthermore, the hydrolysis step itself is carried out in not more than 2 hours, while hydrolysis in the protocol described in U.S. Pat. No. 6,780,841 requires 2 to 10 hours, and preferably about 6 hours (column 5, lines 59-63).

This hydrolysis step is crucial in the process according to the invention. Not only does it save time, but it is also useful to obtain particular characteristics of the hydrolysate according to the invention. Such effects (time saving and obtaining a particular hydrolysate) are obtained due to the use of a proteolytic enzyme at a temperature of between 65 and 75° C., and preferably between 70° C. and 72° C. Advantageously, the proteolytic enzyme is a protease with a broad spectrum for example such as papain, ficin, bromelain or alcalase, and preferable papain or alcalase. Such enzymes are normally used within temperature ranges from 35° C. to 55° C., as described in patent U.S. Pat. No. 6,780,841 (column 5, line 63), temperatures at which their activity is maximum in principle. Therefore the fact that this enzyme is used at 65° C.-75° C. (preferably 70° C.-72° C.) should reduce its activity, and a priori hydrolysis times even longer than the preferred 6 hours in U.S. Pat. No. 6,780,841 should be necessary to obtain a hydrolysate according to the invention with a lower average molecular weight. On the contrary, the inventors surprisingly found that the use of papain at 70° C.-72° C. provides a means of obtaining hydrolysate according to the invention with a maximum hydrolysis time of two hours. The inventors found that under their reaction conditions (raw material and aqueous solution with a pH of between 5.5 and 7.5), the increase in temperature led to faster denaturation of the enzyme but also an increase in its action rate. The temperature interval used (65° C.-75° C., preferably 70° C.-72° C.) corresponds to the best possible ratio between the action rate and the denaturation rate of the enzyme under these usage conditions. This means that the hydrolysis can be performed within duration as little as 1 h00. Advantageously, the hydrolysis duration is between 1 h30 and 2 h, and preferably 2 h00.

Furthermore, the fact that the hydrolysis is done at a higher temperature and within a shorter time (1 h to 2 h at 65-75° C., compared with 2 to 10 h and ideally 6 h at 35-55° C. in patents U.S. Pat. No. 6,025,327, U.S. Pat. No. 6,323,319 and U.S. Pat. No. 6,780,841) results in a saving of time during the process, but also guarantees a good microbiological quality of the product. In particular, this provides a means of avoiding working at critical temperatures (<55° C.) for long periods propitious for the development of pathogenic micro-organisms.

Yet another difference is that the sterilisation step in the process according to the invention is carried just before the product is dried, while in the processes described in patents U.S. Pat. No. 6,025,327, U.S. Pat. No. 6,323,319 and U.S. Pat. No. 6,780,841, it is carried out before the filtering and concentration steps. This also leads to greater health safety of the hydrolysate according to the invention.

Collagens, hexosamines and glycosaminoglycanes (chondroitin sulphate, keratane sulphate, hyaluronic acid) are used as active constituents in human and animal diet food, in human and veterinary pharmacopoeia and in cosmetology. Therefore, the hydrolysate according to the invention can be used in these different applications.

In particular, the invention also relates to hydrolysate according to the invention, possibly obtained by the process according to the invention, for use as a food complement. The invention also relates to hydrolysate according to the invention, possibly obtained by the process according to the invention for use as a medicament.

More particularly, the hydrolysate according to the invention, possibly obtained by the process according to the invention, is advantageously used for treatment or prevention of joint pain. Such joint pain may have various origins, particularly such as degeneration of cartilage related to age, excessive strain of joints due to intensive practice of a sport, excessive strain of joints due to obesity, a degenerative disease of joints such as rheumatoid arthritis, joint defects, osteoarthritis, a cartilage lesion or an auto-immune disease involving antibodies directed against a connective tissue. The hydrolysate according to the invention, possibly obtained according to the invention, is advantageously used for treatment or prevention of joint pain originating from degeneration of the cartilage related to age, excessive strain of joints related to intensive practice of a sport, or an excessive strain of joints related to obesity.

Also advantageously, the hydrolysate according to the invention is used both as a food complement, a source particularly of essential amino acids and constituents of type II collagen, and for treatment of and/or prevention of joint pain in patients already suffering from such pain, or with a risk of development of such pain, particularly due to their age, their previous or present intensive sports habits, or their obesity.

In all previously described applications, the hydrolysate may be present in different forms for different routes of administration. For medical applications or as a food supplement, the hydrolysate is preferably in the form of a powder, either in capsules or compressed in tablets, or ready to be dissolved in an aqueous solution, all of these formulations being suitable for oral administration.

The advantages of the invention are presented in greater detail in FIG. 1 and in the following examples.

EXAMPLES

Example 1

Figure 1:
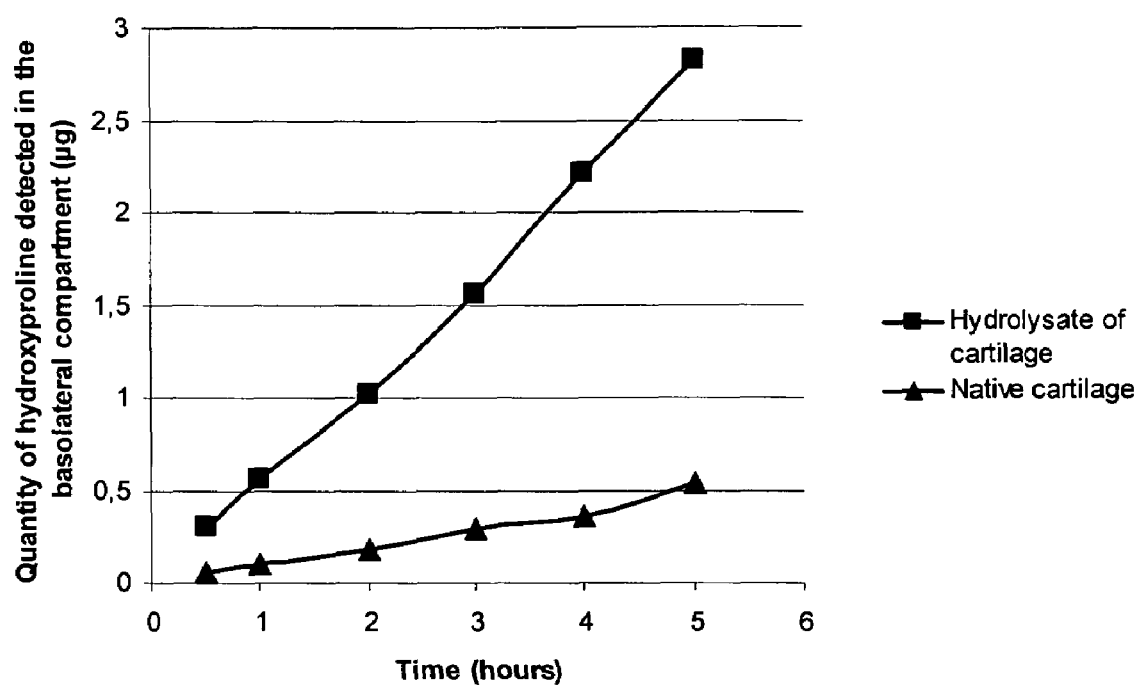
FIG. 1. Bioavailability of the hydrolysate according to the invention compared with non-hydrolysed cartilage (dried and ground chicken sternum, also called native cartilage). The quantity of hydroxyproline (in μg) detected in the compartment on the other side of the cell mat from the compartment in which the products are deposited is shown as a function of time (hours) for the hydrolysate according to the invention and for non-hydrolysed cartilage.

Bioavailability Study for Chicken Cartilage Hydrolysate According to the Invention

An in vitro bioavailability study was made on a layer of CaCo2 cells miming the wall of the intestine. The purpose of this study is to show that active constituents of chicken cartilage hydrolysate according to the invention actually pass through the intestinal barrier.

1.1 Protocols Used

The test used mimes the hydrolysis that occurs on products during ingestion (proteasic and/or amylasic action). In this test, chicken cartilage hydrolysate according to the invention is compared with non-hydrolysed cartilage (dried and ground chicken sternum, also called native cartilage).

In practice, a known quantity of product (hydrolysate according to the invention, non-hydrolysed cartilage) is deposited adjacent to a mat of CaCo2 cells miming the wall of the intestine.

The quantity of product that passes to the other side of the cell mat is then evaluated at different times starting from the deposit. The passage is evaluated by analysis of hydroxyproline (collagen tracer component that is one of the major constituents of the cartilage).

An apparent permeability calculation (Papp) in cm/s is then carried out for each extract, so that the product bioavailabilities can be compared with each other.

1.2 Results

The results obtained clearly show that the in vitro bioavailability of the hydrolysate according to the invention is almost 3 times greater than the non-hydrolysed cartilage, as shown in Table 2 below and in FIG. 1.

TABLE 2

Apparent permeability (Papp) of the hydrolysate according to the invention and the non-hydrolysed cartilage, in cm/s.

| Product | Papp (cm/s) |
| --- | --- |
| hydrolysate according to the invention | $3.99 \times 10^{-6}$ |
| non-hydrolysed cartilage | $1.46 \times 10^{-6}$ |

The value of Papp in the hydrolysate according to the invention suggests an in-vivo acceptable bioavailability, because Gres and al (8) consider that with the CaCo2 line, a Papp of more than $2 \times 10^{-6}$ cm/s could give rise to a human bioavailability of up to 100%.

Example 2

Study of the In Vivo Therapeutic Efficiency of Chicken Cartilage Hydrolysate According to the Invention in Patients Suffering from Joint Pain

A double blind study of the hydrolysate according to the invention compared with the control product was carried out with a group of volunteers complaining of joint pain for 6 months or longer. The two products (hydrolysate according to the invention or a placebo control product) were consumed for three months and their efficiency in reducing joint discomfort was studied.

2.1 Equipment and Methods

2.1.1 Test Substance

2.1.1.1. Product Under Test

The product under test is chicken cartilage hydrolysate according to the invention as described in the description. The hydrolysate is packaged in capsules.

2.1.1.2 Control Product

A second product without any active substance (composed of microcrystalline cellulose, rice starch, vitamin B2, magnesium stearate) presented in the same form (capsules) was used as the control product.

2.1.1.3 Daily Dose

The daily dose of consumed product was fixed at 1500 mg for the test, providing 180 mg of chondroitin sulphate and 975 mg of type II collagen for the hydrolysate according to the invention. The normally recommended daily dose of chondroitin sulphate is 1200 mg.

2.1.2 Volunteers

2.1.2.1. Recruiting Principle

A volunteer recruitment and selection procedure was created to guarantee that the volunteers would be provided with clear and precise information about the study.

2.1.2.2 Inclusion Criteria

The rhumatologist chose the volunteers to be included based on the following criteria:
- person who has given clear, informed consent in writing,
- cooperative person, fully informed about the need and the duration of checkups,
- person between 50 and 75 years old,
- person suffering from joint discomfort for at least 6 months.

2.1.2.3 Non-inclusion Criteria

The non-inclusion criteria were as follows:
- person following an anti-arthritic treatment,
- person with another systemic medical treatment currently or terminated less than one month earlier, that could influence the intensity of joint discomfort,
- person using a food complement that could influence joint discomfort: currently or terminated less than one month earlier,
- person suffering from a serious or advancing disease,
- person consuming alcohol or tobacco immoderately.

2.1.2.4 Associated Treatments

Non-steroidal anti-inflammatory treatments and antalgics were authorised throughout this duration of the test and their exact consumption was marked in the observation book.

Topical skin treatments were authorised for short durations and consumption was noted in the observation book.

Local infiltrations were not allowed.

2.1.3 Evaluation Criteria

2.1.3.1. Consumption of Non-steroidal Anti-inflammatory Drugs

Since volunteers were allowed to consume non-steroidal anti-inflammatory drugs and antalgics freely, they automatically adapted their consumption so as to maintain their pain at an acceptable level at all times.

Therefore a reduction in the consumption of anti-inflammatory drugs indicates a reduction in the pain to be corrected. Since no other treatment was authorised, this reduction can be assigned to the effect of the product being tested on cartilage, leading to a reduction in inflammation and joint pain.

Therefore, the efficiency of the chicken cartilage hydrolysate according to the invention was evaluated by monitoring the quantity of this type of treatment taken.

2.1.3.2 General Health Condition and Usual Daily Movements

At the end of each test period, volunteers described their general health condition and the ease of performing their usual daily movements based on an analogue visual scale (then translated to a scale varying from 0 to 10).

2.1.4 Experimental Plan

The test took place during a total period of 9 months comprising two test periods of 3 months each separated by a three-month rest period.

The study was done in cross over, in other words persons in group 1 tested the control product during the first period and the chicken cartilage hydrolysate according to the invention during the second period, while persons in group 2 tested the chicken cartilage hydrolysate according to the invention during the first period and the control product during the second period. The study took place in double blind, in other words neither the experimenter nor the volunteer was aware of the identification of the products.

2.2 Results 2.2.1 Description of the Sample 37 volunteers were included in the study after a medical examination to locate genes and to measure the intensity at several points.

5 volunteers were taken out of the study (protocol not begun or taking prohibited drugs).

32 volunteers followed the protocol completely and correctly—25 women and 7 men with an average age of 60 years +/−6.

2.2.2 Consumption of Non-steroidal Treatments

An analysis of the observation books shows that the consumption of non-steroidal inflammatory products is significantly higher during the period in which the control product is taken (average consumption=18.1 days (+/−21.7)), compared with the period during which chicken cartilage hydrolysate according to the invention is taken (average consumption=4.9 days (+/−8.3)).

Distributions of the number of treatment days per volunteer for each tested product were determined using the nonparametric Wilcoxon rank test. The significant threshold obtained is $p=0.006<<0.05$ (5% being the value traditionally used for the maximum authorised risk of concluding that there is a difference whereas in fact there is no difference.

Therefore, the statistical analysis demonstrated that the consumption of NSAID per volunteer during the period in which chicken cartilage hydrolysate according to the invention was taken, was significantly less than the consumption during the period in which the control product was taken.

2.2.3 General Health Condition and Usual Daily Movements

On average, volunteers considered that their usual daily movements and their general health condition were better after consuming chicken cartilage hydrolysate according to the invention.

21% of volunteers even indicated that their general health condition was very much improved after taking chicken cartilage hydrolysate according to the invention, compared with only 9% of volunteers who consumed the control product.

2.2.4 Acceptability and Tolerance of Cartilage Hydrolysate Described in the Invention Volunteers found the product very practical in use with an average mark of 4.3 out of 5 (+/−0.8), and believe that the form of the product (capsules) is appropriate to <<food complement>> type use: average mark 3.8 out of 5 (+/−1.0).

Only 7 volunteers complained about minor secondary effects during the period of consumption of chicken cartilage hydrolysate according to the invention.

2.3 CONCLUSION

The purpose of this study was to evaluate the efficiency of chicken cartilage hydrolysate according to the invention, with persons complaining about joint discomfort.

A test at home was carried out during a 9-month period with a group of 32 volunteers. The study took place in double blind in comparison with a control product, with two test periods with a duration of three months each, separated by a three-month rest period. The daily dose of chicken cartilage hydrolysate according to the invention taken by the volunteers was 1500 mg. The volunteers were obliged to see a rhumatologist at the beginning and end of each test period.

The performances of chicken cartilage hydrolysate according to the invention were evaluated by monitoring consumption of anti-inflammatory non-steroidal treatments. The acceptability and tolerance were determined at the end of each test period through a questionnaire.

The check on the consumption of non-steroidal anti-inflammatory products during the test showed that consumption was significantly less during the period in which chicken cartilage hydrolysate according to the invention was taken than during the period in which the control product was taken, thus demonstrating that the chicken cartilage hydrolysate according to the invention has an action on cartilage, leading to a reduction of inflammation and joint pain.

Furthermore, considering the low daily dose of chondroitin sulphate added by chicken cartilage hydrolysate according to the invention (180 mg compared with the 1200 mg normally recommended), the results obtained suggest a synergic effect of hydrolysed type II collagen with the characteristics defined in the description (average molecular weight and composition of amino acids), and chondroitin sulphate.

The evaluation that volunteers made about their usual daily movements and their general health condition at the end of each period using an analogue visual scale showed that both of these points were better when they had been taking chicken cartilage hydrolysate according to the invention rather than the control product. The volunteers judged that chicken cartilage hydrolysate according to the invention was practical in use (mark equal to 4.3 out of 5) and no major secondary effects were felt.

Therefore, chicken cartilage hydrolysate according to the invention can reduce joint discomfort and improve the mobility of joints in patients suffering from chronic joint pain, without leading to severe secondary effects like those induced by non-steroidal anti-inflammatory products.

BIBLIOGRAPHY

1. Eggersgluss, B. (1999). "Gelatine hydrolyste and its health aspects." The European Food & Drink Review (Autumn 1999): 45-49.
2. Yamato, R. and Y. Sakai (2005). Beneficial effects of Tripeptide collagen (HACP) on bones and tendons [translation of a Japanese article]." Foods and Foods Ingredients Journal of Japan 210 (9): 854-858.

3. Blumenkrantz, N. and G. Asboe-Hansen (1978). "Hydroxyproline to hydroxylysine molar ratio indicates collagen type." Acta Dermatovener (Stockolm) 58: 111-115.
4. Barnet M. L., Combitchi D., Trentham D. E. A pilot trial of oral type II collagen in the treatment of juvenile rheumatoid arthritis. Arthritis & Rheumatism. 1996; 39 [4]: 623-628.
5. Bamet, Kremer J. M., St. Clair E. W., Clegg D. O. and al. Treatment of rheumatoid arthritis with oral type II collagen. Arthritis & Rheumatism, 1998; 41 [2]: 290-297.
6. Sieper J. and al. Oral type II collagen treatment in early rheumatoid arthritis. Arthritis & Rheumatism. 1996; 39 [1]: 41-51.
7. Trentham D E, Dynesius-Trentham R A, Orav E J, Combitchi D, Lorenzo C, Sewell K L, Hafler D A, Weiner HL. Effects of Oral Administration of Type II Collagen on Rheumatoid Arthritis. Science. 1993; 261: 1727-1930.
8. Grès, M. C., B. Julian, and al. (1998). "Correlation between oral drug absorption in humans, and apparent drug permeability in TC-7 cells, a human epithelial intestinal cell line: comparison with the parental Caco-2 cell line." Pharmaceutical research 15: 726-733.

The invention claimed is:

1. A hydrolysate of avian cartilage comprising a peptidic fraction and glycosaminoglycans, wherein:
   a) it comprises:
      45% to 70% by weight of hydrolysed type II collagen,
      9% to 15% by weight of chondroitin sulphate,
      0.5% to 2% by weight of hyaluronic acid;
   b) said peptidic fraction comprises:
      2.7% to 3.3% by weight of valine,
      2.0% to 2.4% by weight of isoleucine,
      2.2% to 2.6% by weight of phenylalanine,
      3.8% to 4.2%, by weight of lysine
      0.4% to 0.6% by weight of tryptophane,
      5.5% to 8.7% by weight of hydroxyproline,
      0.7% to 1.8% by weight of hydroxylysine,
      and the molar ratio of hydroxyproline to hydroxylysine is between 5.0 and 8.0;
   c) the average molecular weight of said peptidic fraction is between 500 and 1000 Daltons.

2. The hydrolysate according to claim 1, wherein it is prepared from a mix of 70%-100% by weight of bone and joint cartilage and 0%-30% by weight of sternum cartilage.

3. A process for preparing a hydrolysate of avian cartilage according to claim 1, comprising:
   a) supplying a raw material composed of 70%-100% by weight of bone and joint cartilage (including sternal) and 0%-30% by weight of sternum cartilage,
   b) mixing this raw material with an aqueous solution with a pH between 5.5 and 7.5,
   c) hydrolysing the mix of raw material in water with a proteolytic enzyme during 1 hour to 2 hours, preferably during 1 hour and 30 minutes to 2 hours, at a temperature between 65° C. and 75° C.,
   d) inactivating the proteolytic enzyme for 10 to 20 minutes at least 85° C.,
   e) filtering the reaction mix containing the hydrolysate,
   f) concentrating the reaction mix,
   g) performing final sterilization of the reaction mix at about 130° C. for at least about 30 seconds, and
   h) drying the reaction mix to obtain the hydrolysate in powder form.

4. A food complement comprising the hydrolysate according to claim 1.

5. A medicament comprising the hydrolysate according to claim 1.

6. A method for treating joint pain, comprising administering to a patient an effective amount of the hydrolysate according to claim 1.

7. The method according to claim 6, wherein the origin of joint pain is degeneration of cartilage related to age, excessive strain of joints due to intensive practice of a sport, or excessive strain of joints due to obesity.

* * * * *

UNITED STATES PATENT AND TRADEMARK OFFICE
CERTIFICATE OF CORRECTION

PATENT NO. : 7,671,041 B2  Page 1 of 1
APPLICATION NO. : 11/455239
DATED : March 2, 2010
INVENTOR(S) : Eric Vouland and Céline Berger It is certified that error appears in the above-identified patent and that said Letters Patent is hereby corrected as shown below:

Title Page; item (75); after having checked the Letters Patent, it appears that there is a typographical error in the first name of one of the inventors --Cäcüëline-- The correct spelling is Céline BERGER, in the above-mentioned Patent.

Signed and Sealed this

Third Day of August, 2010

David J. Kappos
*Director of the United States Patent and Trademark Office*